United States Patent [19]

Ikura et al.

[11] Patent Number: 4,713,396

[45] Date of Patent: Dec. 15, 1987

[54] BENZOYLUREA DERIVATIVES

[75] Inventors: Katsuyata Ikura, Ninomiya; Kenji Hagiwara; Fumihiko Nagasaki, both of Odawara; Tomio Yamada; Hidemitsu Takahashi, both of Hiratsuka; Renpei Hatano, Ohiso, all of Japan

[73] Assignee: Nippon Soda Co., Ltd., Tokyo, Japan

[21] Appl. No.: 773,933

[22] Filed: Sep. 9, 1985

[30] Foreign Application Priority Data

Sep. 20, 1984 [JP] Japan ................. 59-195804

[51] Int. Cl.$^4$ .............. C07C 157/12; C07C 127/22; A01N 47/34
[52] U.S. Cl. ..................... 514/594; 514/584; 564/23; 564/44
[58] Field of Search ............ 564/44, 23; 514/584, 514/594

[56] References Cited

U.S. PATENT DOCUMENTS 4,013,717  3/1977  Wellinga et al. ............... 564/44
4,085,226  4/1978  Sirrenberg et al. ............. 564/44
4,276,310  6/1981  Sirrenberg et al. ............. 564/44
4,533,676  8/1985  Sirrenberg et al. ............. 564/44

FOREIGN PATENT DOCUMENTS 23884   2/1981   European Pat. Off. ............ 564/44
93977   11/1983  European Pat. Off. ............ 564/44
3217619 11/1983  Fed. Rep. of Germany ........ 564/44

Primary Examiner—Anton H. Sutto
Assistant Examiner—Carolyn S. Greason
Attorney, Agent, or Firm—George B. Oujevolk

[57] ABSTRACT

A compound having the formula

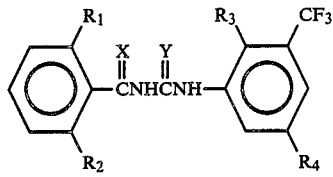

wherein
$R_1$ represents halogen or methyl;
$R_2$ represents hydrogen or halogen;
each of $R_3$ and $R_4$ represents halogen; and
each of X and Y represents oxygen or sulfur.

The compound is useful as insecticide.

12 Claims, No Drawings

BENZOYLUREA DERIVATIVES

The present invention relates to benzoylurea derivatives, insecticidal compositions in the form of a mixture of such compounds with inert carriers, and a process for the production of such compounds.

According to the first aspect of the present invention, there is provided a compound having the formula:

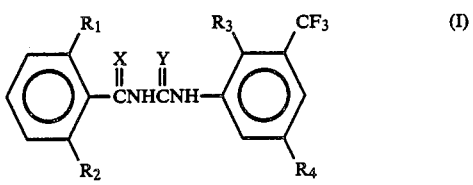

wherein
$R_1$ represents halogen or methyl;
$R_2$ represents hydrogen or halogen;
each of $R_3$ and $R_4$ represents halogen; and
each of X and Y represents oxygen or sulfur.

According to the second aspect of the present invention, there is provided an insecticidal composition comprising an inert carrier and an effective amount of the compound having the formula (I).

It is widely known that N-benzoyl-N'-phenylurea derivatives have insecticidal activity.

As typical commercial insecticides of the said benzoylphenylurea derivatives, those of N-2,6-difluorobenzoyl-N'-4-chlorophenylurea (diflubenzuron) are disclosed in U.S. Pat. No. 3,933,908.

As the compounds similar to the present invention, i.e., the benzoylphenylureas having trifluoromethyl at 3-position of the anilino part and halogen(s) on the phenyl ring(s) of anilino and/or benzoyl part(s) thereof are known as exemplified below:

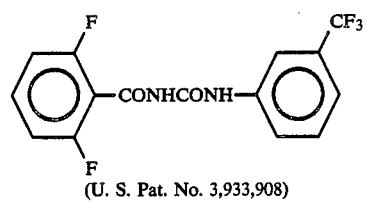

(U. S. Pat. No. 3,933,908)

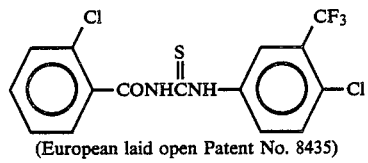

(European laid open Patent No. 8435)

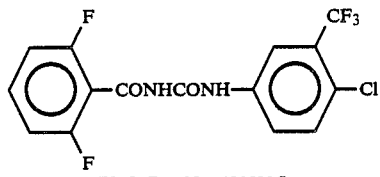

(U. S. Pat. No. 4085226)

The compound having the formula (I) is novel, because the formula (I) itself defined by using the definitions of $R_1$, $R_2$, $R_3$, $R_4$, X and Y as aforesaid and a specific compound contained in the scope defined by said formula (I) are unknown even though said similar compounds and the more general formulae having broader meaning than formula (I) are known, and such compound has a superior insecticidal activity in comparison with the said known compounds and further, has a broader insecticidal spectrum. Furthermore, it possesses excellent insecticidal activity against lepidopterous insects, which are difficult to control because of poor activity of known, similar compounds, and has a low toxicity to haematothermal animals to be used in safety.

According to the third aspect of the invention, there is provided a process for the production of the compound having the formula (I), comprising the step of reaction as illustrated by the following schemes:

A. In case X being oxygen;

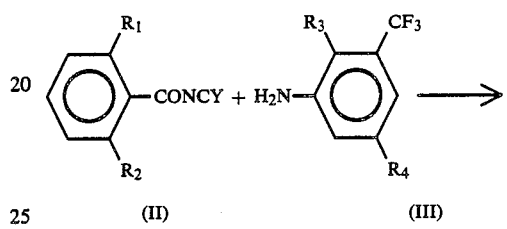

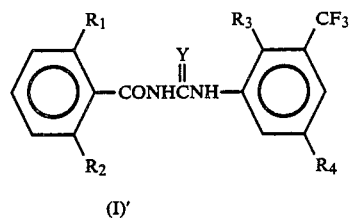

B. In case X and Y being sulfur or oxygen respectively;

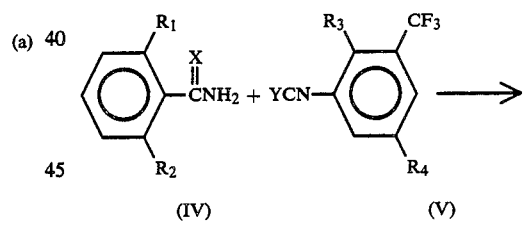

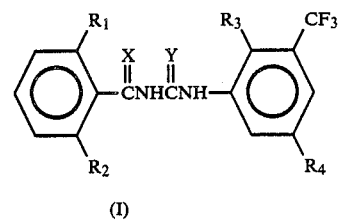

C. In case X being sulfur and Y being oxygen;

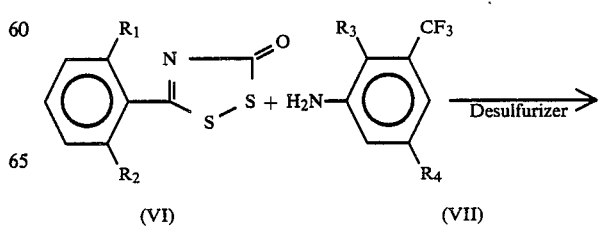

2,5-dihalo-3-trifluoromethylanilines of the formula (III) can be prepared in accordance with the following schemes (a) and (b):

(a) In case $R_3$ and $R_4$ being halogen;

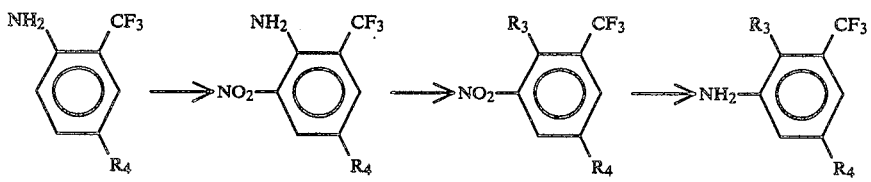

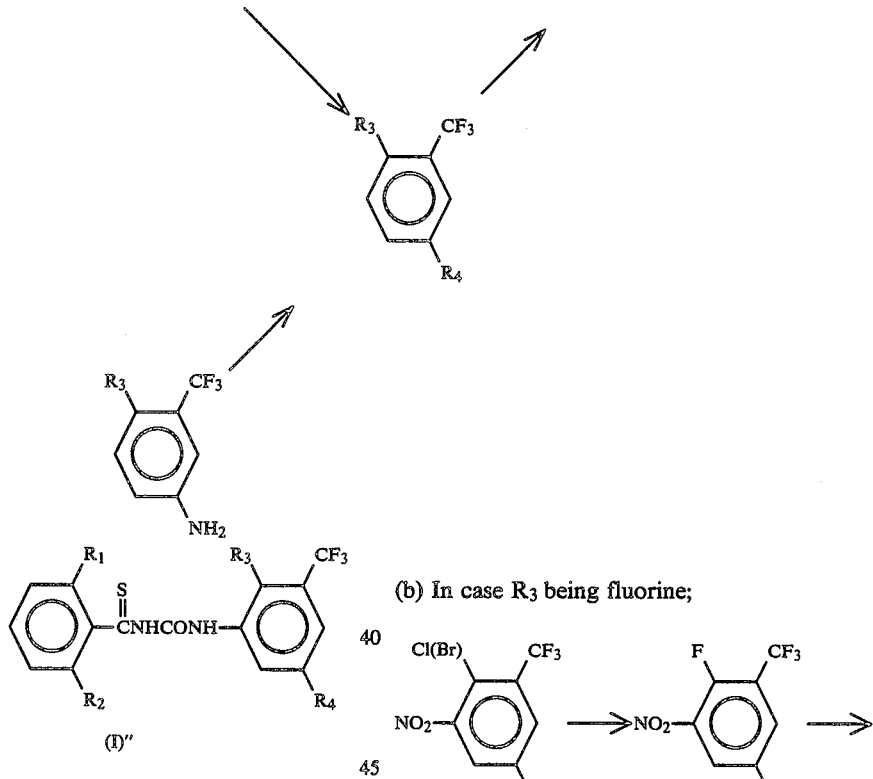

(b) In case $R_3$ being fluorine;

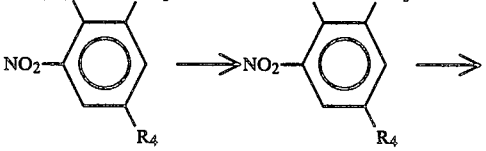

The reactions shown by above schemes A and B are carried out in an organic solvent at a temperature of 0° to 150° C. for 30 minutes to 10 hours. As the solvent, inert organic solvent, for example, benzene, toluene, xylene, pyrydine or the like may be used. To facilitate the reaction, triethylamine, pyridine, or other base may be added as catalyst.

The reaction shown by above scheme C is carried out in the presence of a desulfurizer in inert organic solvent, for example, dichloromethane, chloroform, etc. for 30 minutes to 10 hours at a temperature of 0° C. to the boiling point of the solvent, desirably from 0° C. to room temperature. As the desulfurizer, ordinary agents can be used, but it is desiable to employ tributylphosphine, triphenylphosphine, trimethylphosphine or other trivalent phosphorus compounds.

After the reaction, the compound may be obtained by a usual procedure of the separation and then purified by a conventional purifing procedure such as recrystallization, column chromatography, etc.

A chemical structure of the obtained compound was determined by means of NMR spectrum, Mass spectrum or IR spectrum.

The following Examples illustrate the invention.

EXAMPLE 1

1-(2,5-dichloro-3-trifluoromethylphenyl)-3-(2,6-difluorobenzoyl) urea (Compound No. 1)

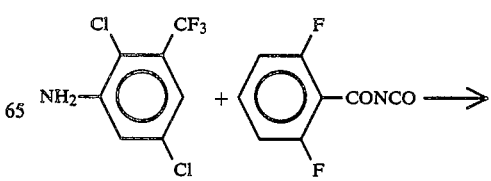

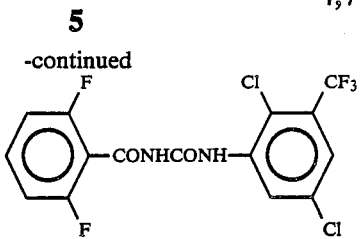

To a solution of 2,5-dichloro-3-trifluoromethyl aniline (0.6 g) in 10 ml of dry benzene was added dropwise a solution of 2,6-difluorobenzoylisocyanate (0.5 g) in 5 ml of dry benzene under water-cooling and the solution was stirred for one hour at room temperature. 50 ml of n-hexane was added to the above solution and the precipitated crystal was filtered. The crystal was washed with n-hexane to obtain the desired product 0.9 g. (m.p. 205°–207.5° C.)

EXAMPLE 2

1-(5-chloro-2-fluoro-3-trifluoromethylphenyl)-3-(2,6-difluorobenzoyl) urea (Compound No. 4)

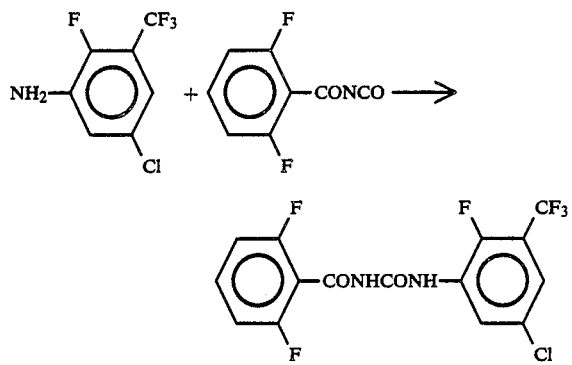

The product was prepared from 5-chloro-2-fluoro-3-trifluoromethylaniline (0.5 g) and 2,6-difluorobenzoylisocyanate (0.4 g) by operating according to the process of Example 1 to obtain the product 0.6 g. (m.p. 187°–189° C.)

EXAMPLE 3

1-(2,5-dichloro-3-trifluoromethylphenyl)-3-(2,6-difluorobenzoyl) thiourea (Compound No. 15)

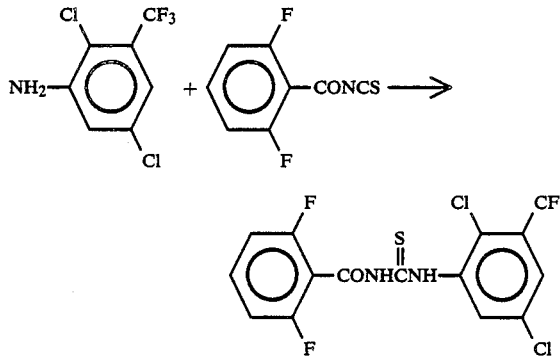

To a solution of 2,5-dichloro-3-trifluoromethylaniline (0.5 g) in 10 ml of dry benzene was added a solution of 2,6-difluorobenzoylisothiocyanate (0.45 g) in 5 ml of dry benzene under water-cooling and the solution was stirred for 10 hours. The benzene was then distilled off under reduced pressure and the residue was washed with n-hexane to obtain the desired product 0.6 g. (m.p. 136°–141° C.)

EXAMPLE 4

1-(2,5-dichloro-3-trifluoromethylphenyl)-3-(2,6-difluorothiobenzoyl) urea (Compound No. 25)

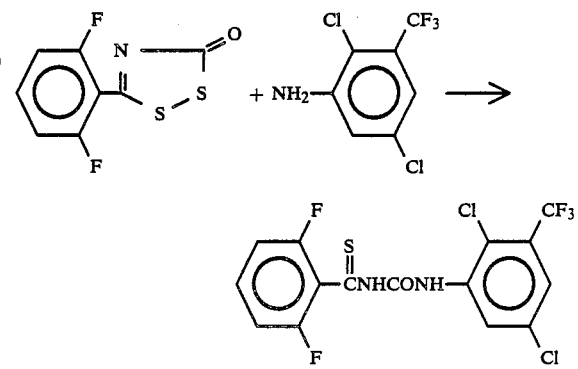

To a solution of 5-(2,6-difluorophenyl)-1,2,4-dithiazole-3-one (0.9 g) in 20 ml of dichloromethane was added dropwise a solution of 2,5-dichloro-3-trifluoromethylaniline (0.9 g) and tributylphosphine (0.8 g) in 10 ml of dichloromethane under ice-cooling and the solution was stirred for 30 minutes at room temperature. The dichloromethane was then distilled off under reduced pressure and to the residue was added ligroin. The precipitated crystal was filtered and the crystal was washed with ligroin to obtain the desired product 1.3 g. (d.p. 176°–177° C.)

Inclusive of the above, each compound within the scope of the invention, which can be prepared in an analogous manner, is tabulated in Table 1.

TABLE 1

| Compound No. | $R_1$ | $R_2$ | $R_3$ | $R_4$ | X | Y | Physical Properties ( ): m.p. °C. |
|---|---|---|---|---|---|---|---|
| 1 | F | F | Cl | Cl | O | O | (205–207.5) |
| 2 | Cl | H | " | " | " | " | (190–194) |
| 3 | Br | " | " | " | " | " | (191–194) |
| 4 | F | F | F | " | " | " | (187–189) |
| 5 | Cl | H | " | " | " | " | (156–160) |
| 6 | Br | " | " | " | " | " | (132–137) |
| 7 | F | Cl | Cl | " | " | " | (227.5–229) |
| 8 | " | " | F | " | " | " | (194–199) |
| 9 | CH$_3$ | H | Cl | " | " | " | (192–193) |
| 10 | " | " | F | " | " | " | (193–195) |
| 11 | F | " | Cl | " | " | " | (180–183.5) |
| 12 | " | " | F | " | " | " | (167–169) |
| 13 | " | F | Cl | Br | " | " | (197–199) |
| 14 | Cl | H | " | " | " | " | (170–171) |
| 15 | F | F | Cl | Cl | " | S | (136–141) |
| 16 | " | " | F | " | " | " | (94–99) |
| 17 | " | Cl | Cl | " | " | " | (135–139) |
| 18 | " | " | F | " | " | " | (126–130) |
| 19 | Cl | H | Cl | " | " | " | (143–146) |
| 20 | " | " | F | " | " | " | (114–117) |
| 21 | CH$_3$ | " | Cl | " | " | " | (146–148) |
| 22 | " | " | F | " | " | " | (106–109) |
| 23 | Br | " | Cl | " | " | " | (149–154) |
| 24 | " | " | F | " | " | " | (125–130) |
| 25 | F | F | Cl | " | S | O | (176–177) d.p. |
| 26 | Cl | H | " | " | " | " | (181–182) |
| 27 | CH$_3$ | " | " | " | " | " | (170–173) |

TABLE 1-continued $$\underset{R_2}{\underset{|}{\overset{R_1}{\overset{|}{\bigcirc}}}}-\overset{X}{\overset{\|}{C}}NH\overset{Y}{\overset{\|}{C}}NH-\underset{R_4}{\underset{|}{\overset{R_3}{\overset{|}{\bigcirc}}}}-CF_3$$

| Compound No. | $R_1$ | $R_2$ | $R_3$ | $R_4$ | X | Y | Physical Properties ( ): m.p. °C. |
|---|---|---|---|---|---|---|---|
| 28 | F | Cl | " | " | " | " | (178–182) |
| 29 | Br | H | " | " | " | " | (175–177) |
| 30 | F | F | F | " | " | " | (173) d.p. |
| 31 | Cl | H | " | " | " | " | (173) d.p. |
| 32 | CH₃ | " | " | " | " | " | (151–153) |
| 33 | Cl | " | " | " | " | S | |
| 34 | F | F | " | " | " | " | |
| 35 | " | H | " | " | " | O | (160–162) |
| 36 | " | F | Cl | Br | " | " | (180) d.p. |
| 37 | Cl | H | " | " | " | " | (169–171) |
| 38 | F | " | " | Cl | " | " | (178–180) |
| 39 | " | F | Br | " | O | " | (208–211) |
| 40 | " | " | Cl | F | " | " | (226–229) |
| 41 | " | " | Br | Cl | " | S | (161–164) |
| 42 | " | " | Cl | F | " | " | (163–166) |
| 43 | " | " | F | " | " | O | (163–168) |
| 44 | " | " | " | " | S | " | (181–183) d.p. |
| 45 | " | H | " | " | " | " | (170–171) d.p. |
| 46 | " | F | Cl | " | " | " | (177–179) |
| 47 | " | H | " | " | " | " | (180–181) d.p. |

As already mentioned, the compound having the formula (I) exhibits an outstanding insecticidal efficacy and an insecticidal composition containing the compound as an active ingredient may be formulated by mixing suitable carrieres in a form generally used in agricultural pesticide, such as wettable powder, emulsifiable concentrate, dust, granular formulation, suspension concentrate or the like.

As solid carriers, cereal flours such as soy bean flour and wheat flour, ground minerals such as diatomaceous earth, apatite, gypsum, talc, bentonite and clay, and organic or inorganic compounds such as sodium benzonate, urea and sodium sulfate may be used.

As liquid carriers, vegetable oil, mineral oil, petroleum such as kerosine, solvent naphtha, and xylene, cyclohexane, cyclohexanone, dimethylformamide, dimethylsulfoxide, trichloroethylene, methylisobutyl ketone and water may be used.

A surfactant may, if necessary, be added in order to give a homogeneous and stable formulation.

The concentration of the active ingredient in an insecticidal composition may vary according to type of formulation, and is, for example, in the range of 5–70 weight percent, preferably 10–30 weight percent, in wettable powder; 5–30 weight percent, preferably 10–20 weight percent, in emulsifiable concentrate; 1–10 weight percent, preferably 2–5 weight percent in dust; 5–40 weight percent, preferably 10–30 weight percent in suspension concentrate; 1–10 weight percent, preferably 2–5 weight percent in granular formulation.

The wettable powder, the emulsifiable concentrate, and suspension concentrate are diluted with water to the specified concentrations and used as a liquid suspension or a liquid emulsion to spray over the plants.

The dust and granular formulation are directly used for spraying over the plants.

Examples of the insecticidal composition of this invention are as mentioned below, but the scope of the invention shall not be limited to those:

EXAMPLE 5

Emulsifiable Concentrate

| | |
|---|---|
| Compound of this invention | 10 parts by weight |
| Calcium dodecylbenzenesulfonate | 5 parts by weight |
| Dimethylformamide | 40 parts by weight |
| Xylene | 40 parts by weight |
| Polyoxyethylene styrylphenyl ether | 3 parts by weight |
| Polyoxyethylene alkylaryl ether | 2 parts by weight |

Those are mixed together to provide an emulsifiable concentrate containing 10% of active ingredient. In use, it is diluted with water to the desired concentration of the emulsion.

EXAMPLE 6

Wettable Powder

| | |
|---|---|
| Compound of this invention | 20 parts by weight |
| Talc | 75 parts by weight |
| Sodium lignin sulfonate | 3 parts by weight |
| Sodium stearate | 2 parts by weight |

Those are mixed together to provide a wettable powder containing 20% of active ingredient. In use, it is diluted with water to the desired concentration of the suspension.

EXAMPLE 7

Suspension Concenterate

| | |
|---|---|
| Compound of this invention | 20 parts by weight |
| Oxyethylenated polyarylphenol phosphate nutralized with amine | 2 parts by weight |
| Xanthan gum | 0.2 parts by weight |
| Water | 77.8 parts by weight |

Those are mixed to provide a suspension concentrate containing 20% of active ingredient. In use, it is diluted with water to obtain a suspension at the desired concentration.

EXAMPLE 8

Dust

| | |
|---|---|
| Compound of this invention | 5 parts by weight |
| Talc | 92 parts by weight |
| Silica | 3 parts by weight |

Those are mixed together to provide a dust containing 5% of active ingredient.

Further, it goes without saying that the compound indicates a sufficient insecticidal efficacy, but, in the insecticidal composition, one kind or two kinds or more of other insecticidal compounds may be mixed in order to give a rapid insecticidal action or extend its spectrum (hereinafter called "mixed composition") because the compound of this invention indicates a slow-acting effect on larva.

In the mixed composition, the compound can be used with one kind or two kinds or more of fungicidal and/or acaricidal compound(s) as well as the insecticidal compound having the rapid action.

Typical examples of insecticidal compounds usable together with the compound of this invention in the mixed composition as active ingredient(s) are set forth below:

(Organophosphorous compounds or carbamates)
  fenthion, fenitrotion, diazinon, chlorpyrifos, ESP, vamidothion, phenthoate, dimethoate, formotion, malathion, trichlorfon, thiomethon, dichlorvos, acephate, cyanophos, pyrimiphos methyl, isoxathion, pyridaphenthion, DMTP, prothiophos, sulfprofos, profenofos, CVMP, salithion, EPN, CYP, aldicarb, propoxur, pyrimicarb, methomyl, cartap, carbaryl, thiodicarb, carbosulfen, carbosulfan, nicotine.

(Pyrethoroids)
  permethrin, cypermethrin, decamethrin, fenvalerate, fenpropathrin, cyhalothrin, flucythrate, fencyclate, tetramethrin, cyfluthrin, fluvalinate, pyrethrin, allethrin, tetramethrin, resmethrin, barthrin, dimethrin, propathrin, prothrin.

The insectidical activity of the compound is illustrated by the following tests.

TEST 1

Insectidical activity against Tobacco cutworm

A wettable powder formulated according to the aforesaid Example was diluted with water to the specified concentrations of the compound.

A leaf of sweet potato was immersed in the chemical solution for 30 seconds and air-dried.

The treated leaf was put in a petri dish of 9 cm diameter in which 5 third instar larvae of tobacco cutworm were released and the petri dish was capped with a sheet of glass. The petri dish was placed in a room at 25° C. and 65% relative humidity, and the mortality was investigated after 120 hours and 95% lethal concentration value ($LC_{95}$) was obtained. The results are shown in Table 2.

TABLE 2

| Compound No. | $LC_{95}$ (ppm) |
| --- | --- |
| 1 | 0.17 |
| 2 | 0.18 |
| 3 | 0.33 |
| 4 | 0.10 |
| 5 | 0.20 |
| 6 | 0.50 |
| 7 | 0.70 |
| 8 | 0.20 |
| 11 | 0.70 |
| 12 | 0.65 |
| 13 | 0.27 |
| 14 | 0.72 |
| 15 | 0.65 |
| 16 | 0.055 |
| 17 | 0.16 |
| 18 | 0.22 |
| 19 | 0.18 |
| 20 | 0.18 |
| 23 | 0.97 |
| 24 | 0.86 |
| 25 | 0.58 |
| 26 | 0.21 |
| 29 | 0.64 |
| 31 | 0.92 |
| 36 | 0.20 |
| 37 | 0.058 |
| 39 | 0.33 |
| 40 | 0.26 |
| 41 | 0.22 |
| 42 | 0.20 |
| 43 | 0.13 |
| Comparative Compound A* | 5.20 |
| Comparative Compound B | 64.0 |
| Comparative Compound C | 164 |

TABLE 2-continued

| Compound No. | $LC_{95}$ (ppm) |
| --- | --- |
| Comparative Compound D | 170 |

Comparative Compound A:

$$\text{F-}\bigcirc\text{-CONHCONH-}\bigcirc\text{-CF}_3$$
(with F on first ring)

Comparative Compound B:

$$\text{Cl-}\bigcirc\text{-CONHCNH-}\bigcirc\text{-Cl}$$
(with S=, CF$_3$)

Comparative Compound C:

$$\text{F-}\bigcirc\text{-CONHCONH-}\bigcirc\text{-Cl}$$
(diflubenzuron)

Comparative Compound D:

$$\text{F,F-}\bigcirc\text{-CONHCONH-}\bigcirc\text{-Cl,Cl}$$

TEST 2

Insecticidal activity against Armyworm

An emulsifiable concentrate or a wettable powder formulated according to the aforesaid Examples was diluted with water to the specified concentrations of the compound. A leaf of corn was immersed in the chemical solution for 30 seconds and air-dried. The treated leaf was put in a petri dish enclosing 5 third instar larvae of the armyworm, and the petri dish was capped with a sheet of glass. The petri dish was placed in a room kept at 25° C. and 65% relative humidity, and the mortality was investigated after 120 hours and $LC_{95}$ was obtained. The results are shown in Table 3.

TABLE 3

| Compound No. | $LC_{95}$ (ppm) |
| --- | --- |
| 1 | 0.21 |
| 2 | 1.00 |
| 4 | 0.21 |
| 5 | 0.25 |
| 6 | 0.34 |
| 7 | 0.32 |
| 8 | 0.35 |
| 11 | 0.70 |
| 12 | 0.61 |
| 13 | 0.27 |
| 14 | 0.33 |
| 15 | 0.85 |
| 16 | 0.29 |
| 17 | 0.32 |
| 18 | 0.73 |
| 19 | 0.91 |
| 20 | 0.68 |
| 25 | 0.27 |
| 26 | 0.82 |
| 30 | 0.87 |
| 31 | 0.70 |
| 36 | 0.28 |
| 37 | 0.80 |
| 38 | 0.80 |
| 39 | 0.27 |
| 40 | 0.068 |
| 41 | 0.27 |

TABLE 3-continued

| Compound No. | LC$_{95}$ (ppm) |
| --- | --- |
| 42 | 0.007 |
| 43 | 0.14 |
| Comparative Compound A* | 10.6 |
| Comparative Compound B | >125 |
| Comparative Compound D | 51 |
| Comparative Compound E | 11.0 |

*Comparative compound A, B and D are the same as shown as Table 2.

*Comparative Compound E: 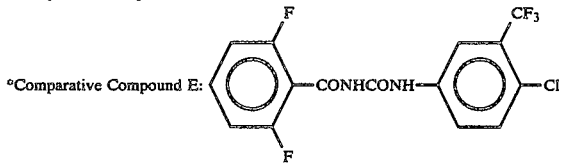

TEST 3

Insecticidal activity against Diamondback moth

An emulsifiable concentrate or a wettable powder was diluted with water to the specified concentrations of the compound.

A leaf of cabbage was immersed in the chemical solution for 30 seconds and air-dried.

The treated leaf was put in a petri dish of 9 cm diameter in which 5 third instar larvae of dimondback moth were released, and the petri dish was capped with a sheet of glass. The petri dish was kept in a room at 25° C. and 65% relative humidity, and the mortality was investigated after 120 hours and LC$_{95}$ was obtained. The results are shown in Table 4.

TABLE 4

| Compound No. | LC$_{95}$ (ppm) |
| --- | --- |
| 1 | 0.27 |
| 2 | 0.96 |
| 3 | 0.23 |
| 4 | 0.35 |
| 5 | 0.18 |
| 6 | 0.33 |
| 11 | 0.34 |
| 12 | 0.21 |
| 15 | 0.34 |
| 16 | 0.34 |
| 19 | 0.92 |
| 20 | 0.32 |
| 26 | 0.27 |
| 43 | 0.072 |
| Comparative Compound | |
| *B | 18.0 |

TABLE 4-continued

| | LC$_{95}$ (ppm) |
| --- | --- |
| C | >500 |
| D | >125 |
| E | 8.0 |

*All comparative compounds are the same as shown as Table 2 or Table 3.

What we claim is:

1. A compound having the formula

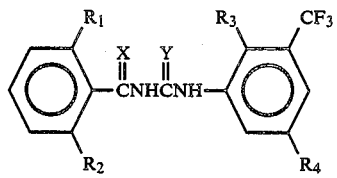

wherein
$R_1$ represents halogen or methyl;
$R_2$ represents hydrogen or halogen;
each of $R_3$ and $R_4$ represents halogen; and
each of X and Y represents oxygen or sulfur but both are not sulfur.

2. As a compound of claim 1, 1-(2,5-dichloro-3-trifluoromethylphenyl)-3-(2,6-difluorobenzoyl) urea.

3. As a compound of claim 1, 1-(5-chloro-2-fluoro-3-trifluoromethylphenyl)-3-(2,6-difluorobenzoyl) urea.

4. As a compound of claim 1, 1-(2-chloro-5-fluoro-3-trifluoromethylphenyl)-3-(2,6-difluorobenzoyl) urea.

5. As a compound of claim 1, 1-(2,5-difluoro-3-trifluoromethylphenyl)-3-(2,6-difluorobenzoyl) urea.

6. As a compound of claim 1, 1-(2,5-dichloro-3-trifluoromethylphenyl)-3-(2-fluorobenzoyl) urea.

7. An insecticidal composition comprising an inert carrier and an effective amount of a compound of claim 1.

8. An insecticidal composition comprising an inert carrier and an effective amount of a compound of claim 2.

9. An insecticidal composition comprising an inert carrier and an effective amount of a compound of claim 3.

10. An insecticidal composition comprising an inert carrier and an effective amount of a compound of claim 4.

11. An insecticidal composition comprising an inert carrier and an effective amount of a compound of claim 5.

12. An insecticidal composition comprising an inert carrier and an effective amount of a compound of claim 6.

* * * * *